(12) United States Patent
Gormley et al.

(10) Patent No.: US 9,902,994 B2
(45) Date of Patent: Feb. 27, 2018

(54) METHOD FOR RETAINING EVEN COVERAGE OF SHORT INSERT LIBRARIES

(71) Applicant: Illumina Cambridge Limited, Nr Saffron Walden (GB)

(72) Inventors: Niall Anthony Gormley, Nr Saffron Walden (GB); Melanie Anne Smith, Nr Saffron (GB)

(73) Assignee: ILLUMINA CAMBRIDGE LIMITED, Little Chesterford, Nr Saffron Walden (GB)

( * ) Notice: Subject to any disclaimer, the term of this patent is extended or adjusted under 35 U.S.C. 154(b) by 365 days.

(21) Appl. No.: 14/559,548

(22) Filed: Dec. 3, 2014

(65) Prior Publication Data
US 2015/0119292 A1 Apr. 30, 2015

Related U.S. Application Data

(62) Division of application No. 11/895,294, filed on Aug. 23, 2007, now Pat. No. 8,932,994.

(60) Provisional application No. 60/840,063, filed on Aug. 24, 2006.

(51) Int. Cl.
*C12Q 1/68* (2006.01)

(52) U.S. Cl.
CPC .................. *C12Q 1/6855* (2013.01)

(58) Field of Classification Search
None
See application file for complete search history.

(56) References Cited

U.S. PATENT DOCUMENTS

| | | | |
|---|---|---|---|
| 6,287,825 B1 | 9/2001 | Weissman et al. | |
| 2004/0067493 A1 | 4/2004 | Matsuzaki et al. | |
| 2004/0209299 A1 | 10/2004 | Pinter et al. | |

FOREIGN PATENT DOCUMENTS

| | | |
|---|---|---|
| GB | 2412170 | 9/2005 |
| WO | 2005/082098 A2 | 9/2005 |
| WO | 2007/052006 | 5/2007 |
| WO | 2007060456 | 5/2007 |

OTHER PUBLICATIONS

Andersson, Bjorn et al., "A Double Adaptor method for improved shotgun library construction", Analytical Biochemistry vol. 236 1996, 1996, 107-113.
Cheung, et al., "Whole genome amplification using a degenerate oligonucleotide primer allows hundreds of genotypes to be performed on less than one nanogram of genomic DNA", PNAS, 93, 1996, 14676-14679.
Epicenter End-It (TM), "DNA repair kit instruction sheet", www.EpiBio.com Lit # 153 Sep. 2010, 2010, 4.
Gilar, Martin et al., "Study of phosphorothioate-modified oligonucleotide resistance to 3'-exonucleoase using capillary electrophoresis", Journal of Chromatography B, vol. 714 No. 1, Aug. 28, 1998, 13-20.
Hengen, , 1995 available on line at / schneider.ncicrf.gov/methods/TIBS/feb95.txt downloaded Apr. 9, 2014, 1995.
Lizardi, , "Mutation detection and single-molecule counting using isothermal rolling-circle amplification", Nature Genetics, vol. 19, 1998, 225-232.
Margulies, et al., "Genome sequencing in microfabricated high-density picolitre reactors", Nature, vol. 437, 2005, 376-380 and Supplemental Materials.
Roychoudhury, et al., Nucleic Acids Reserach 3, 1976, 101-116.
Shendure, et al., "Accurate Multiplex Polony Sequencing of an Evolved Bacterial Genome", Science, vol. 309, Sep. 9, 2005, 1728-1732.

*Primary Examiner* — Christopher M Gross

(57) ABSTRACT

The invention relates to a method of preparing a library of template polynucleotides with uniform sequence representation and to use of a library of templates prepared using this method for solid-phase nucleic acid amplification. In particular, the invention relates to a method of preparing a library of template polynucleotides which have common sequences at their 5' ends and at their 3' ends, which contains even representation of all the fragments present in a starting sample of nucleic acid before fragmentation. The invention is especially applicable to the preparation of short insert libraries, where the sample fragments are less than 150 base pairs in length.

21 Claims, 3 Drawing Sheets

Figure 1 Overview of protocol:

SEQUENCE LISTING

<160> NUMBER OF SEQ ID NOS: 20

<210> SEQ ID NO 1
<211> LENGTH: 33
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (32)..(33)
<223> OTHER INFORMATION: Linkage between nucleotide 32 and 33 is
      phosphorothioate bond

<400> SEQUENCE: 1
acactctttc cctacacgac gctcttccga tct                                33

<210> SEQ ID NO 2
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 2
gatcggaaga gctcgtatgc cgtcttctgc ttg                                33

<210> SEQ ID NO 3
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 3
aatgatacgg cgaccaccga gatctacact ctttccctac acga                    44

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

```
<400> SEQUENCE: 4
caagcagaag acggcatacg a                                              21

<210> SEQ ID NO 5
<211> LENGTH: 148
<212> TYPE: DNA
<213> ORGANISM: Homo sapiens

<400> SEQUENCE: 5
aatgatacgg cgaccaccga gatctacact ctttccctac acgacgctct tccgatctga    60
gacggggttt caccgtttta gccgggatgg tctcgatctc ctgacctcgt gatcagatcg   120
gaagagctcg tatgccgtct tctgcttg                                     148

<210> SEQ ID NO 6
<211> LENGTH: 141
<212> TYPE: DNA
<213> ORGANISM: Homo sapiens

<400> SEQUENCE: 6
aatgatacgg cgaccaccga gatctacact ctttccctac acgacgctct tccgatctaa    60
gtttttactg tattttaaga ataagctcgg ccgagcgcgg tggctcaaga tcggaagagc   120
tcgtatgccg tcttctgctt g                                            141

<210> SEQ ID NO 7
<211> LENGTH: 175
<212> TYPE: DNA
<213> ORGANISM: Homo sapiens

<400> SEQUENCE: 7
aatgatacgg cgaccaccga gatctacact ctttccctac acgacgctct tccgatctag    60
ctgcttggga ggctgaggca ggagaatcgc ttgaacctgg gaggcagagt ttgcagtgag   120
cagagattat gccactgcac tagatcggaa gagctcgtat gccgtcttct gcttg       175

<210> SEQ ID NO 8
<211> LENGTH: 161
<212> TYPE: DNA
<213> ORGANISM: Homo sapiens

<400> SEQUENCE: 8
aatgatacgg cgaccaccga gatctacact ctttccctac acgacgctct tccgatctaa    60
gaggctggaa gcagaagagg tttcagaccc agatccctcc tttcagaaaa ccccccaaac   120
tgaaccaaga tcggaagagc tcgtatgccg tcttctgctt g                      161

<210> SEQ ID NO 9
<211> LENGTH: 176
<212> TYPE: DNA
<213> ORGANISM: Homo sapiens

<400> SEQUENCE: 9
aatgatacgg cgaccaccga gatctacact ctttccctac acgacgctct tccgatctca    60
tcaacttgtg taccttgtaa ctgtaccaca acaggtattt taatttccaa acttttact    120 gccatgacta tacccttgc tgagatcgga agagctcgta tgccgtcttc tgcttg       176

<210> SEQ ID NO 10
<211> LENGTH: 156
<212> TYPE: DNA
<213> ORGANISM: Homo sapiens
```

-continued

```
<400> SEQUENCE: 10
aatgatacgg cgaccaccga gatctacact ctttccctac acgacgctct tccgatcttt      60
agtgtcccag aaagatgaac tatttccctt ctctacttgg tctgcccatt tctacttcct     120
gcagatcgga gagctcgta tgccgtcttc tgcttg                                 156

<210> SEQ ID NO 11
<211> LENGTH: 154
<212> TYPE: DNA
<213> ORGANISM: Homo sapiens

<400> SEQUENCE: 11
aatgatacgg cgaccaccga gatctacact ctttccctac acgacgctct tccgatcttc      60
actattgttg cccaggctgg agtgcagtgg tgcaatctcg gctcactgca acttccgcct     120
agatcggaag agctcgtatg ccgtcttctg cttg                                  154

<210> SEQ ID NO 12
<211> LENGTH: 134
<212> TYPE: DNA
<213> ORGANISM: Homo sapiens

<400> SEQUENCE: 12
aatgatacgg cgaccaccga gatctacact ctttccctac acgacgctct tccgatcttg      60
ggattacagg catgagccac cacgcctggc tgtatttgtt agatcggaag agctcgtatg     120
ccgtcttctg cttg                                                        134

<210> SEQ ID NO 13
<211> LENGTH: 151
<212> TYPE: DNA
<213> ORGANISM: Homo sapiens

<400> SEQUENCE: 13
aatgatacgg cgaccaccga gatctacact ctttccctac acgacgctct tccgatcttc      60
cttctgcttt tttcttcact cgtttcccca cagagcaaga caaaagaagc cggcaagaga     120
tcggaagagc tcgtatgccg tcttctgctt g                                    151

<210> SEQ ID NO 14
<211> LENGTH: 155
<212> TYPE: DNA
<213> ORGANISM: Homo sapiens

<400> SEQUENCE: 14
aatgatacgg cgaccaccga gatctacact ctttccctac acgacgctct tccgatctgc      60
gggtatgaac agttcgccta cgacggcaag gattatctca ccctgaatga ggacctgcgc     120
tagatcggaa gagctcgtat gccgtcttct gcttg                                155

<210> SEQ ID NO 15
<211> LENGTH: 167
<212> TYPE: DNA
<213> ORGANISM: Homo sapiens

<400> SEQUENCE: 15
aatgatacgg cgaccaccga gatctacact ctttccctac acgacgctct tccgatcttt      60
tccacacatg ctgaagtttt caagatttga tcattgccta gtattttcat tttcttactt     120
tccgtgaacc ttaagatcgg aagagctcgt atgccgtctt ctgcttg                   167
```

```
<210> SEQ ID NO 16
<211> LENGTH: 132
<212> TYPE: DNA
<213> ORGANISM: Homo sapiens

<400> SEQUENCE: 16
aatgatacgg cgaccaccga gatctacact ctttccctac acgacgctct tccgatctac      60
aaaagaaatc ggctgggcat gatgcattca tctgtagtag atcggaagag ctcgtatgcc     120
gtcttctgct tg                                                         132

<210> SEQ ID NO 17
<211> LENGTH: 150
<212> TYPE: DNA
<213> ORGANISM: Homo sapiens

<400> SEQUENCE: 17
aatgatacgg cgaccaccga gatctacact ctttccctac acgacgctct tccgatctag      60
tattttattg aggattttg cattgatgtt catcagggat attggcttaa attttcagat      120
cggaagagct cgtatgccgt cttctgcttg                                      150

<210> SEQ ID NO 18
<211> LENGTH: 122
<212> TYPE: DNA
<213> ORGANISM: Homo sapiens

<400> SEQUENCE: 18
aatgatacgg cgaccaccga gatctacact ctttccctac acgacgctct tccgatctca      60
ccaccacacc tggctaattt tatattttag atcggaagag ctcgtatgcc gtcttctgct     120
tg                                                                    122

<210> SEQ ID NO 19
<211> LENGTH: 139
<212> TYPE: DNA
<213> ORGANISM: Homo sapiens

<400> SEQUENCE: 19
aatgatacgg cgaccaccga gatctacact ctttccctac acgacgctct tccgatctta      60
ttgtagaagg tatcaaagag gaataagctc tccagcttgc acagaagatc ggaagagctc     120
gtatgccgtc ttctgcttg                                                  139

<210> SEQ ID NO 20
<211> LENGTH: 124
<212> TYPE: DNA
<213> ORGANISM: Homo sapiens

<400> SEQUENCE: 20
caagcagaag acggcatacg agctcttccg atcttccagc ctgggcgaca gagcaagact      60
cggcctagat cggaagagcg tcgtgtaggg aaagagtgta gatctcggtg gtcgccgtat     120
catt                                                                  124
```

METHOD FOR RETAINING EVEN COVERAGE OF SHORT INSERT LIBRARIES

FIELD OF THE INVENTION

The invention relates to a method of preparing a library of template polynucleotides with uniform sequence representation. The invention also relates to the use of a library of templates prepared using the method of the invention for solid-phase nucleic acid amplification. In particular, the invention relates to a method of preparing a library of template polynucleotides which have common sequences at their 5' ends and at their 3' ends, and contains even representation of all the fragments in the original sample before fragmentation. The invention is especially applicable to the preparation of short insert libraries, where the sample fragments are less than 150 base pairs in length.

BACKGROUND OF THE INVENTION

Several publications and patent documents are referenced in this application in order to more fully describe the state of the art to which this invention pertains. The disclosure of each of these publications and documents is incorporated by reference herein.

The ability to acquire and analyse DNA sequence data has increased phenomenally over the past few years. As a result nucleic acid analysis has become increasingly important in many areas of biology, biotechnology and medicine. Molecular biology and pharmaceutical drug development now make intensive use of nucleic acid analysis. The most challenging areas are whole genome sequencing, single nucleotide polymorphism detection, screening and gene expression monitoring, which typically require generation and analysis of large amounts of nucleic acid sequence data.

One area of technology which revolutionised the study of nucleic acids was the development of nucleic acid amplification techniques, such as the polymerase chain reaction (PCR). Amplification reactions, such as PCR, can enable the user to specifically and selectively amplify a particular target nucleic acid of interest from a complex mixture of nucleic acids. However, there is also an ongoing need for nucleic acid amplification techniques which enable simultaneous amplification of complex mixtures of templates of diverse sequence, such as genomic DNA fragments (e.g. 'whole genome' amplification) or cDNA libraries, in a single amplification reaction.

PCR amplification cannot occur in the absence of annealing of forward and reverse amplification primers to primer binding sequences in the template to be amplified under the conditions of the annealing steps of the PCR reaction, i.e. if there is insufficient complementarity between primers and template. Some prior knowledge of the sequence of the template is therefore required before one can carry out a PCR reaction to amplify a specific template, unless random primers are used with a consequential loss of specificity. The user must usually know the sequence of at least the primer-binding sites in the template in advance so that appropriate primers can be designed, although the remaining sequence of the template may be unknown. The need for prior knowledge of the sequence of the template increases the complexity and cost of PCR amplification of complex mixtures of templates, such as genomic DNA fragments.

Several of the new methods employed for high throughput DNA sequencing (*Nature*. 437, 376-380 (2005); *Science*. 309, 5741, 1728-1732 (2005)) rely on a universal amplification reaction, whereby a DNA sample is randomly fragmented, then treated such that the ends of the different fragments all contain the same DNA sequence. Fragments with universal ends can be amplified in a single reaction with a single pair of amplification primers. Separation of the library of fragments to the single molecule level prior to amplification ensures that the amplified molecules form discrete populations that can then be further analysed. Such separations can be performed either in emulsions (*Nature*. 437, 376-380 (2005); *Science*. 309, 5741, 1728-1732 (2005)), or on a surface (Nucleic Acids Research 27, e34 (1999); Nucleic Acids Research 15, e87 (2000)).

WO 98/44151 and WO 00/18957 both describe methods of forming polynucleotide arrays based on 'solid-phase' nucleic acid amplification, which is a bridging amplification reaction wherein the amplification products are immobilised on a solid support in order to form arrays comprised of nucleic acid clusters or 'colonies'. Each cluster or colony on such an array is formed from a plurality of identical immobilised polynucleotide strands and a plurality of identical immobilised complementary polynucleotide strands. The arrays so-formed are generally referred to herein as 'clustered arrays' and their general features will be further understood by reference to WO 98/44151 or WO 00/18957, the contents of both documents being incorporated herein in their entirety by reference.

In common with all amplification techniques, solid-phase bridging amplification requires the use of forward and reverse amplification primers which include 'template-specific' nucleotide sequences which are capable of annealing to sequences in the template to be amplified, or the complement thereof, under the conditions of the annealing steps of the amplification reaction. The sequences in the template to which the primers anneal under conditions of the amplification reaction may be referred to herein as 'primer-binding' sequences.

Certain embodiments of the methods described in WO 98/44151 and WO 00/18957 make use of 'universal' primers to amplify templates comprising a variable template portion that it is desired to amplify flanked 5' and 3' by common or 'universal' primer binding sequences. The 'universal' forward and reverse primers include sequences capable of annealing to the 'universal' primer binding sequences in the template construct. The variable template portion, or 'target' may itself be of known, unknown or partially known sequence. This approach has the advantage that it is not necessary to design a specific pair of primers for each target sequence to be amplified; the same primers can be used for amplification of different templates provided that each template is modified by addition of the same universal primer-binding sequences to its 5' and 3' ends. The variable target sequence can therefore be any DNA fragment of interest. An analogous approach can be used to amplify a mixture of templates (targets with known ends), such as a plurality or library of target nucleic acid molecules (e.g. genomic DNA fragments), using a single pair of universal forward and reverse primers, provided that each template molecule in the mixture is modified by the addition of the same universal primer-binding sequences.

Such 'universal primer' approaches to PCR amplification, and in particular solid-phase bridging amplification, are advantageous since they enable multiple template molecules of the same or different, known or unknown sequence to be amplified in a single amplification reaction, which may be carried out on a solid support bearing a single pair of 'universal' primers. Simultaneous amplification of a mixture of templates of different sequences would otherwise require a plurality of primer pairs, each pair being complementary to each unique template in the mixture. The generation of a plurality of primer pairs for each individual template is not a viable option for complex mixtures of templates.

The addition of universal priming sequences onto the ends of targets to be amplified by PCR can be achieved by a variety of methods known to those skilled in the art. For example, a universal primer consisting of a universal sequence at its 5' end and a degenerate sequence at its 3' end can be used in a PCR (DOP-PCR, e.g., PNAS 1996 vol 93 pg 14676-14679) to amplify fragments randomly from a complex target sequence or a complex mixture of target sequences. The degenerate 3' portion of the primer anneals at random positions on DNA and can be extended to generate a copy of the target that has the universal sequence at its 5' end.

Alternatively, adaptors that contain universal priming sequences can be ligated onto the ends of the target sequences. The adaptors may be single-stranded or double-stranded. If double-stranded, they may have overhanging ends that are complementary to overhanging ends on the target molecules that may have been generated by digestion with a restriction endonuclease, or added with a DNA polymerase or terminal transferase. Alternatively, the double-stranded adaptors may be blunt, in which case the targets are also blunt ended. The blunt ends of the targets may have been formed during a process to shear the DNA into fragments, or they may have been formed by an end repair reaction, as would be well known to those skilled in the art.

A single adaptor or two different adaptors may be used in a ligation reaction with target sequences. If a target has been manipulated such that its ends are the same, i.e. both are blunt or both have the same overhang, then ligation of a single compatible adaptor will generate a template with that adaptor on both ends. However, if two compatible adaptors, adaptor A and adaptor B, are used, then three permutations of ligated products are formed: template with adaptor A on both ends, template with adaptor B on both ends, and template with adaptor A on one end and adaptor B on the other end. This last product is, under some circumstances, the only desired product from the ligation reaction and consequently additional purification steps are necessary following the ligation reaction to purify it from the ligation products that have the same adaptor at both ends.

In the preparation of libraries for universal amplification, it is advantageous to make the insert region as short as possible. Such 'short insert libraries', where the primary nucleic acid sample is fragmented so that the average length of the target inserts is less than 150 base pairs, are advantageous for minimising the amount of sample DNA required in short read sequencing, and to minimise the size of amplified clusters. Short insert libraries minimise the amount of nucleic acid needed; for example sequencing 25 bases of a 100 base pair fragment, means 25% of the sample DNA is sequenced, whereas if the length of the fragments is 250 bases, only 10% of the material is sequenced, and more DNA is required to obtain the same amount of information about the sample. Longer fragments also give larger clusters when amplified on a surface, reducing the number of features than can be packed into an array of a finite size.

A major drawback in current methods for library construction is that the steps of the method are carried out under conditions that can denature some of the target fragments. This problem becomes acute when the fragments are short, and can result in the loss of fragments with a high level of A/T base pairs (which are weaker than G/C basepairs) from the library. The library is therefore not representative of the original sample.

SUMMARY OF THE INVENTION

The present method differs from those of the prior art in that it is performed at lower temperatures, less than 65° C., which thereby ensures that all the fragments in the library remain as a duplex independent of sequence composition, and therefore the distribution of sequences of the target regions in the library of adaptor-target-adaptor polynucleotides is representative of all the sequences contained in the original primary sample. The method as performed does not result in the loss of the A/T rich (G/C poor) fragments from the library (i.e. A/T rich fragments are retained in the library), and the library therefore retains a full coverage of every nucleic acid base in the original, unfragmented, primary nucleic acid.

A first aspect of the invention provides a method of preparing a library of adaptor-target-adaptor constructs, said method comprising:
(a) preparing a plurality of target polynucleotide duplex fragments having a distribution of sequences;
(b) treating the plurality of target polynucleotide duplex fragments to phosphorylate the 5' ends of each of the plurality of target polynucleotide duplex fragments and to incorporate at least one nucleotide overhang at each of the 3' ends of each of the plurality of target polynucleotide duplex fragments, wherein the treating is performed at a temperature of less than 65° C. and produces a plurality of modified target polynucleotide duplex fragments and wherein the plurality of modified target polynucleotide duplex fragments is purified at a temperature of less than 65° C.; and
(c) ligating adaptor polynucleotides to both ends of each of the plurality of modified target polynucleotide duplex fragments to produce a library of adaptor-target-adaptor constructs;
wherein the distribution of sequences of the target polynucleotide duplex fragments in the library of adaptor-target-adaptor constructs is essentially equal to the distribution of sequences of the target polynucleotide duplex fragments.

A second aspect of the invention relates to a library prepared by the method of the first aspect of the invention, wherein the fragments average less than 150 base pairs in length.

A third aspect of the invention provides a method of solid-phase nucleic acid amplification of template polynucleotide molecules which comprises: preparing a library of template polynucleotide molecules which have common sequences at their 5' ends and common sequences at their 3' ends using the method according to the first aspect of the invention and carrying out a solid-phase amplification reaction wherein said template polynucleotide molecules are amplified.

A fourth aspect of the invention provides an array comprising amplified single molecules of the library of template polynucleotides prepared according to the first aspect of the invention.

A fifth aspect of the invention provides for use of the array according to the fourth aspect of the invention in sequencing.

A sixth aspect of the invention provides for the use of a population of adaptor-target-adaptor constructs prepared according to the first aspect of the invention.

DETAILED DESCRIPTION OF THE INVENTION

Figure 1:
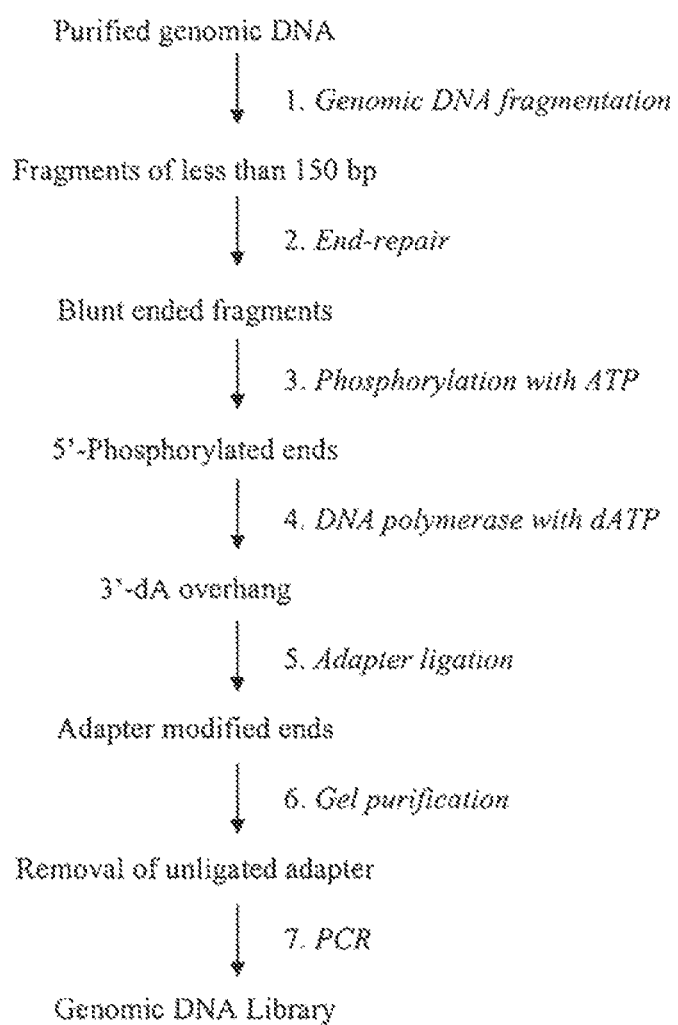
FIG. 1 shows a schematic of steps of the method as described.

The invention relates to a method of preparing a library of adaptor-target-adaptor polynucleotide constructs wherein the distribution of sequences of the target fragments in the library is representative of or parallels that of the distribution of the sequences of the target polynucleotide fragments in the original sample. The distribution of sequences of the target fragments in the library of adaptor-target-adaptor polynucleotide constructs is, therefore, essentially equal to the distribution of the sequences of the target polynucleotide fragments in the original sample. Where the distribution of fragments is said to be essentially equal to the distribution in the library, this means that each base in the target sequence is represented in the library independent of sequence context of the fragment. The term 'essentially equal' means that the variation between the sequences present in the original target sample and the sequences contained in the library of adapter-target-adapter sequences is minimised such that less than 10% of the sequences are lost from the sample, with at least 90% of the sequences being retained in the resultant library. More particularly, the losses are less than 1%, with 99% of the target fragment sequences being retained in the resultant library. This does not mean that 99% of the material needs to be captured in the library, merely that at least 99% of the sequences present in the target sample need to be represented in the resultant library.

In the preparation of libraries for universal amplification, it is advantageous to make the insert region as short as possible. Such 'short insert libraries', wherein the primary nucleic acid sample is fragmented so that the average length of the target inserts is less than 150 base pairs, are advantageous in that they minimize the amount of sample DNA required in short read sequencing and minimize the size of amplified clusters. The length of the DNA fragments used in surface-based bridging amplification correlates directly with the size of the clusters grown on the surface, as longer fragments can reach primers further away. For an array of finite physical size, the number of discrete clusters that can be sequenced depends on the size of the clusters. Shorter DNA molecules produce smaller clusters, which therefore increases the number of features that can be sequenced on a single chip.

Short insert libraries also minimize the amount of nucleic acid needed. Sequencing 25 bases of a 100 base pair fragment, for example, means 25% of the sample DNA is sequenced, whereas if the length of the fragments is 250 bases, only 10% of the material is sequenced, and more DNA is required to obtain the same amount of information about the sample. The minimization of the sample DNA required is particularly advantageous under circumstances wherein the amount of sample DNA is limited.

A major drawback in current methods for library construction relates to the fact that the steps of the method are performed under conditions that can denature some of the target fragments. This problem becomes acute when the fragments are short, and can result in the loss of fragments with a high level (e.g. greater than 50%) of A/T base pairs (which are weaker than G/C basepairs) from the library. A library so produced is, therefore, not representative of the original sample, and any subsequent analysis therefore requires a greater depth of sequencing to ensure all the bases in the target sequences are analysed. The depth of sequencing refers to the number of times each base appears in a certain experiment. If, for example, the original fragment is 100,000 bases in length, and the experiment in question generates 1 million bases, each base should be present 10 times, and the depth is said to be 10×. Due to the random nature of the process, however, some bases may appear 25 times or more, and some bases may appear only once or twice. In extreme cases, some bases that were present in the original sample may not appear in the sequence data at all, as they have been lost from the sample. The invention as described herein minimizes the losses of material that arise from the sequence context (e.g., A/T rich content), and ensures that the sequences of the targets in the library that is sequenced is essentially equal to the sequences of the targets in the initial fragmented sample. Such a library is said to the representative of the original sample. A/T rich fragments are fragments that contain a higher than 50% sequence of adenine or thymine bases. It is very rare for a sequence of hundreds bases to contain nothing but A and T bases, but sequences of hundreds of bases of which greater than 85% are A and T are known to exist in biological organisms. These duplexes are easily denatured and lost from the library, and the methods described herein ensure that the fragments with higher than 50% A/T composition, specifically those in the region of 50-85% A/T coverage are not lost from the library (i.e. such sequences are retained in the library).

As explained in further detail below, each of the templates within the library comprises a region of common sequence at (or proximal to) its 5' and 3' end, wherein the common sequence at the 5' end of each individual template in the library is not identical and not fully complementary to the common sequence at the 3' end of each individual template.

The term 'adaptor-target-adaptor library' refers to a collection or plurality of adaptor-target-adaptor molecules which share common sequences at their 5' ends and common sequences at their 3' ends. Use of the term 'adaptor-target-adaptor library' to refer to a collection or plurality of molecules should not be taken to imply that the molecules making up the library are derived from a particular source, or that the 'library' has a particular composition. By way of example, use of the term 'adaptor-target-adaptor library' should not be understood to imply that the individual molecules within the library must be of different nucleotide sequence or that the templates be related in terms of sequence and/or source.

In its various embodiments, the invention encompasses formation of so-called 'monotemplate' libraries, which comprise multiple copies of a single type of molecule, each having common sequences at their 5' ends and their 3' ends, as well as 'complex' libraries wherein many of the individual molecules comprise different target sequences, although all share common sequences at their 5' ends and 3' ends. Such complex libraries may be prepared using the method of the invention starting from a complex mixture of target polynucleotides such as (but not limited to) random genomic DNA fragments, cDNA libraries, etc. The invention also extends to 'complex' libraries formed by mixing together several individual 'monotemplate' libraries, each of which has been prepared separately using the method of the invention starting from a single type of target molecule (i.e., a monotemplate), or libraries made from different 'complex' libraries further pooled. All molecules in a given library will share common sequence at their 5' ends and common sequence at their 3' ends.

Use of the term 'template' to refer to individual polynucleotide molecules in the library merely indicates that one or both strands of the polynucleotides in the library are capable of acting as templates for template-dependent nucleic acid polymerisation catalysed by a polymerase. Use of this term should not be viewed as limiting the scope of the invention to libraries of polynucleotides which are ultimately used as templates in a subsequent enzyme-catalysed polymerisation reaction.

An adaptor-target-adaptor library of the invention is formed by first ligating identical adaptor polynucleotide molecules ('mismatched adaptors', the general features of which are defined below) to the 5' and 3' ends of one or more target polynucleotide duplexes (which may be of known, partially known or unknown sequence) to form adaptor-target constructs. In order to carry out the ligation, the target polynucleotide duplex fragments are treated such that each fragment carries a 5'-phosphate moiety and an overhanging region at the 3'-end. Such treating produces a plurality of modified polynucleotide duplex fragments. All steps in the method are carried out at a temperature of less that 65° C., in the absence of thermophilic enzymes or heat denaturing steps, to ensure that all the target polynucleotide fragments are maintained as duplexes, and are not denatured to single strands. In one embodiment of the method, all steps are carried out at a temperature of less than 40° C.

One of the novel aspects of the present invention relates to the appreciation that the treating to achieve an overhanging region at the 3'-end (i.e., an A-tailing reaction) may be performed using Klenow exonuclease minus (Klenow exo-), rather than a thermophilic polymerase. The use of Klenow exo-facilitates preparation of modified polynucleotide duplex constructs at a temperature of less than 65° C. In order to maintain a temperature of less than 65° C., the modified polynucleotide duplex constructs are purified from the Klenow exo-via column purification in the present method.

As used herein, "distribution of sequences of the target polynucleotide duplex fragments" refers to the stoichiometric relationship of each of the sequences of a plurality of target polynucleotide duplex fragments relative to each other. The representation of any individual fragment within the plurality relates to the number of copies present in the plurality sequences. For genomic fragments, the distribution of fragments is 1:1, with respect to any pair of genomic fragments.

The adaptor-target-adaptor constructs can be copied and amplified by primer extension reactions with primers complementary to the adaptor sequences. The resulting primer extension products, and optionally amplified copies thereof, collectively provide a library of template polynucleotides.

The adaptor polynucleotides used in the method of the invention are referred to herein as 'mismatched' adaptors because, as will be explained in detail herein, it is essential that the adaptors include a region of sequence mismatch, i.e., they must not be formed by annealing of fully complementary polynucleotide strands.

Mismatched adaptors for use in the invention are formed by annealing two partially complementary polynucleotide strands so as to provide, when the two strands are annealed, at least one double-stranded region and at least one unmatched region.

The 'double-stranded region' of the adaptor is a short double-stranded region, typically comprising 5 or more consecutive base pairs, formed by annealing of the two partially complementary polynucleotide strands. This term simply refers to a double-stranded region of nucleic acid in which the two strands are annealed and does not imply any particular structural conformation.

Generally it is advantageous for the double-stranded region to be as short as possible without loss of function. The term 'function' in this context refers to the ability of the double-stranded region to form a stable duplex under standard reaction conditions for an enzyme-catalysed nucleic acid ligation reaction, which conditions are well known to the skilled practitioner (e.g. incubation at a temperature in the range of from 4° C. to 25° C. in a ligation buffer appropriate for the enzyme). In other words, function refers to the ability of the two strands forming the adaptor to remain partially annealed during ligation of the adaptor to a target molecule. It is not absolutely necessary for the double-stranded region to be stable under the conditions typically used in the annealing steps of primer extension or PCR reactions.

Since identical adaptors are ligated to both ends of each template molecule, the target sequence in each adaptor-target construct is flanked by complementary sequences derived from the double-stranded region of the adaptors. The longer the double-stranded region, and hence the complementary sequences derived therefrom in the adaptor-target constructs, the greater the possibility that the adaptor-target construct is able to fold back and base-pair to itself in these regions of internal self-complementarity under the annealing conditions used in primer extension and/or PCR. It is, therefore, generally preferred that the double-stranded region is 20 or less, 15 or less, or 10 or less base pairs in length in order to reduce this effect. The stability of the double-stranded region may be increased, and hence its length potentially reduced, by the inclusion of non-natural nucleotides which exhibit stronger base-pairing than standard Watson-Crick base pairs.

In a particular embodiment, the two strands of the adaptor are 100% complementary in the double-stranded region. It will, however, be appreciated that one or more nucleotide mismatches may be tolerated within the double-stranded region, provided that the two strands are capable of forming a stable duplex under standard ligation conditions.

Adaptors for use in the invention will generally include a double-stranded region forming the 'ligatable' end of the adaptor, i.e., the end that is joined to a target polynucleotide in the ligation reaction. The ligatable end of the adaptor may be blunt or, in other embodiments, short 5' or 3' overhangs of one or more nucleotides may be present to facilitate/promote ligation. The 5' terminal nucleotide at the ligatable end of the adaptor should be phosphorylated to enable phosphodiester linkage to a 3' hydroxyl group on the target polynucleotide.

The term 'unmatched region' refers to a region of the adaptor wherein the sequences of the two polynucleotide strands forming the adaptor exhibit a degree of non-complementarity such that the two strands are not capable of fully annealing to each other under standard annealing conditions for a primer extension or PCR reaction. The unmatched region(s) may exhibit some degree of annealing under standard reaction conditions for a enzyme-catalysed ligation reaction, provided that the two strands revert to single stranded form under annealing conditions in an amplification reaction.

The adaptor constructs may contain exonuclease resistant modifications as described below. Such modifications lower the level of adaptor-dimers present in the library as the two adaptors can not undergo ligation without removal of their non complementary overhangs. The adaptors can be treated with an exonuclease enzyme, as described below, prior to the ligation reaction with the target, to ensure that the overhanging ends of the strands can not be removed during the ligation process. Treatment of the adaptors in this manner reduces the formation of the adaptor-dimers at the ligation step.

Each strand of each template molecule in the library formed in the primer extension reaction will therefore have the following structure, when viewed as a single strand:
5'-[common sequence I]-[target sequence]-[common sequence II]-3'
wherein 'common sequence I' represents a sequence derived from copying a first strand of the mismatched adaptor and is common to all template molecules in the library generated in the initial primer extension reaction; 'target' represents a sequence derived from one strand of the target polynucleotide duplex and may be different in different individual template molecules within the library; and 'common sequence II' represents a sequence derived from copying of a second strand of the mismatched adaptor and is also common to all template molecules in the library generated in the initial primer extension reaction.

Since 'common sequence I' and 'common sequence II' are common to all template strands in the library they may include 'universal' primer-binding sequences, enabling all templates in the library to be ultimately amplified in a solid-phase PCR procedure using universal primers.

It is a key feature of the invention, however, that the common 5' and 3' end sequences denoted 'common sequence I' and 'common sequence II' are not fully complementary to each other, meaning that each individual template strand can contain different (and non-complementary) universal primer sequences at its 5' and 3' ends.

It is generally advantageous for complex libraries of templates to be amplified, for example by PCR or isothermal amplification (e.g. whole genome amplification), either in solution or on a solid support, to include regions of 'different' sequence at their 5' and 3' ends, which are nevertheless common to all template molecules in the library, especially if the amplification products are to be sequenced ultimately. For example, the presence of a common unique sequence at one end only of each template in the library can provide a binding site for a sequencing primer, enabling one strand of each template in the amplified form of the library to be sequenced in a single sequencing reaction using a single type of sequencing primer. The method of the invention may also be applied to the preparation of libraries which are amplified in vivo, such as for example bacterial cDNA libraries and the like.

Typically 'common sequence I' and 'common sequence II' consist of no more than 100, or no more than 50, or no more than 40 consecutive nucleotides at the 5' and 3' ends, respectively, of each strand of each template polynucleotide. The precise length of the two sequences may or may not be identical. The nucleotide sequences of 'common sequence I' and 'common sequence II' in the template polynucleotides are determined in part by the sequences of the adaptor strands ligated to the target polynucleotides and in part by the sequence of the primer used in the initial primer extension reaction, and any subsequent rounds of nucleic acid amplification.

In embodiments wherein the initial primer extension product is subjected to further amplification by conventional PCR, then the products of the amplification reaction are double-stranded polynucleotides, one strand of which has the structure:
5'-[common sequence I]-[target sequence]-[common sequence II]-3'

It will be appreciated that 'common sequence II' in the amplification products may differ somewhat to the 'common sequence II' present in the products of the initial primer extension reaction, since the former is determined in part by the sequence of the PCR primer used to prime synthesis of a polynucleotide strand complementary to the initial primer extension product, whereas the latter will be determined solely by copying of the adaptor sequences at the 3' ends of the adaptor-template constructs in the initial primer extension. Nevertheless, since the PCR primer is designed to anneal to a sequence in the initial extension products which is complementary to the 3' adaptor, the two forms of 'common sequence II' will contain identical sequence, at least at the 3' end. Additional sequence may be included at the 5' end of 'common sequence II' in the amplified products, for example by the use of 'tailed' PCR primers, as described in detail below. In other embodiments the common sequences present in the amplification products may actually be shorter than the common sequences included in the adaptors originally ligated to the target.

The precise nucleotide sequences of the common regions of the template molecules in the library are generally not material to the invention and may be selected by the user. The common sequences must at least comprise 'primer-binding' sequences which enable specific annealing of amplification primers when the templates are in use in a solid-phase amplification reaction. The primer-binding sequences are thus determined by the sequence of the primers to be used for solid-phase amplification. The sequence of these primers in turn is advantageously selected to avoid or minimise binding of the primers to the target portions of the templates within the library under conditions used for the amplification reaction, but is otherwise not particularly limited. By way of example, if the target portions of the templates are derived from human genomic DNA, then the sequences of the primers to be used in solid phase amplification should ideally be selected to minimise non-specific binding to any human genomic sequence.

The conditions encountered during the annealing steps of an amplification reaction will be generally known to one skilled in the art, although the precise annealing conditions will vary from reaction to reaction (see Sambrook et al., 2001, *Molecular Cloning, A Laboratory Manual,* 3rd Ed, Cold Spring Harbor Laboratory Press, Cold Spring Harbor Laboratory Press, NY; Current Protocols, eds Ausubel et al.). Typically such conditions may comprise, but are not limited to, (following a denaturing step at a temperature of about 94° C. for about one minute) exposure to a temperature in the range of from 40° C. to 72° C. (preferably 50-68° C.) for a period of about 1 minute in standard PCR reaction buffer.

Different annealing conditions may be used for a single primer extension reaction, which is not part of a cycle of a PCR reaction (again see Sambrook et al., 2001, *Molecular Cloning, A Laboratory Manual,* 3rd Ed, Cold Spring Harbor Laboratory Press, Cold Spring Harbor Laboratory Press, NY; Current Protocols, eds Ausubel et al.). Conditions for primer annealing in a single primer extension include, for example, exposure to a temperature in the range of from 30 to 37° C. in standard primer extension buffer. It will be appreciated that different enzymes, and hence different reaction buffers, may be used for a single primer extension reaction as opposed to a PCR reaction. There is no requirement to use a thermostable polymerase for a single primer extension reaction.

It is to be understood that the 'unmatched region' is provided by different portions of the same two polynucleotide strands which form the double-stranded region(s). Mismatches in the adaptor construct can take the form of one strand being longer than the other, such that there is a single stranded region on one of the strands, or a sequence selected such that the two strands do not hybridise, and thus form a single stranded region on both strands. The mismatches may also take the form of 'bubbles', wherein both ends of the adaptor construct(s) are capable of hybridising to each other and forming a duplex, but the central region is not. The portion of the strand(s) forming the unmatched region are not annealed under conditions in which other portions of the same two strands are annealed to form one or more double-stranded regions. For avoidance of doubt it is to be understood that a single-stranded or single base overhang at the 3' end of a polynucleotide duplex that subsequently undergoes ligation to the target sequences does not constitute an 'unmatched region' in the context of this invention.

The lower limit on the length of the unmatched region will typically be determined by function, for example the need to provide a suitable sequence for binding of a primer for primer extension, PCR and/or sequencing. Theoretically there is no upper limit on the length of the unmatched region, except that in general it is advantageous to minimise the overall length of the adaptor, for example in order to facilitate separation of unbound adaptors from adaptor-target constructs following the ligation step. Therefore, it is preferred that the unmatched region should be less than 50, or less than 40, or less than 30, or less than 25 consecutive nucleotides in length.

The precise nucleotide sequence of the adaptors is generally not material to the invention and may be selected by the user such that the desired sequence elements are ultimately included in the common sequences of the library of templates derived from the adaptors, for example to provide binding sites for particular sets of universal amplification primers and/or sequencing primers. Additional sequence elements may be included, for example to provide binding sites for sequencing primers which will ultimately be used in sequencing of template molecules in the library, or products derived from amplification of the template library, for example on a solid support. The adaptors may further include 'tag' sequences, which can be used to tag or mark template molecules derived from a particular source. The general features and use of such tag sequences is described in applicant's pending application published as WO 05/068656.

Although the precise nucleotide sequence of the adaptor is generally non-limiting to the invention, the sequences of the individual strands in the unmatched region should be such that neither individual strand exhibits any internal self-complementarity which could lead to self-annealing or formation of hairpin structures, etc. under standard annealing conditions. Self-annealing of a strand in the unmatched region is to be avoided as it may prevent or reduce specific binding of an amplification primer to this strand.

The mismatched adaptors are preferably formed from two strands of DNA, but may include mixtures of natural and non-natural nucleotides (e.g. one or more ribonucleotides) linked by a mixture of phosphodiester and non-phosphodiester backbone linkages. Other non-nucleotide modifications may be included such as, for example, biotin moieties, blocking groups and capture moieties for attachment to a solid surface, as discussed in further detail below.

The method comprises a first step of fragmenting one or more primary polynucleotide molecules to produce target polynucleotide duplexes.

As used herein, the term 'polynucleotide' refers to deoxyribonucleic acid (DNA), but where appropriate the skilled artisan will recognise that the method may also be applied to ribonucleic acid (RNA). The terms should be understood to include, as equivalents, analogs of either DNA or RNA made from nucleotide analogs and to be applicable to single stranded (such as sense or antisense) and double stranded polynucleotides. The term as used herein also encompasses cDNA, that is complementary or copy DNA produced from an RNA template, for example by the action of reverse transcriptase.

The primary polynucleotide molecules may originate in double-stranded DNA (dsDNA) form (e.g. genomic DNA fragments, PCR and amplification products and the like) or may have originated in single-stranded form, as DNA or RNA, and been converted to dsDNA form. By way of example, mRNA molecules may be copied into double-stranded cDNAs suitable for use in the method of the invention using standard techniques well known in the art. The precise sequence of the primary polynucleotide molecules is generally not material to the invention, and may be known or unknown.

In a particular embodiment, the primary polynucleotide molecules are DNA molecules. More particularly, the primary polynucleotide molecules represent the entire genetic complement of an organism, and are genomic DNA molecules which include both intron and exon sequence (coding sequence), as well as non-coding regulatory sequences such as promoter and enhancer sequences. Although it could be envisaged that particular sub-sets of polynucleotide sequences or genomic DNA could also be used, such as particular chromosomes, for example. Yet more particularly, the sequence of the primary polynucleotide molecules is not known. Still yet more particularly, the primary polynucleotide molecules are human genomic DNA molecules. The DNA target molecules may be treated chemically or enzymatically either prior to, or subsequent to any random fragmentation processes, and prior to or subsequent to the ligation of the adaptor sequences.

The sequence of the primary polynucleotide molecules may be the same or different, for example, a mixture of primary polynucleotide molecules of different sequences may be prepared by mixing a plurality of individual primary polynucleotide molecules. For example, DNA from more than one source can be prepared if each DNA sample is first tagged to enable its identification after it has been sequenced. Many different suitable DNA-tag methodologies already exist in the art and are well within the purview of the skilled person.

Random fragmentation refers to the fragmentation of a polynucleotide molecule in a non-ordered fashion by enzymatic, chemical or mechanical means. Such fragmentation methods are known in the art and utilise standard methods (Sambrook and Russell, Molecular Cloning, A Laboratory Manual, third edition). For the sake of clarity, generating smaller fragments of a larger piece of nucleic acid via specific PCR amplification of such smaller fragments is not equivalent to fragmenting the larger piece of nucleic acid because the larger piece of nucleic acid sequence remains intact (i.e., is not fragmented by the PCR amplification). The random fragmentation is designed to produce fragments irrespective of the sequence identity or position of nucleotides comprising and/or surrounding the break. More particularly the random fragmentation is by mechanical means such as nebulisation or sonication to produce fragments of about 50 base pairs in length to about 1500 base pairs in length, still more particularly 50 to 700 base pairs in length, yet more particularly 50-400 base pairs in length. Most particularly, the method is used to generate smaller fragments of from 50-150 base pairs in length.

Fragmentation of polynucleotide molecules by mechanical means (nebulization, sonication and Hydroshear for example) results in fragments with a heterogeneous mix of blunt and 3'- and 5'-overhanging ends. It is therefore desirable to repair the fragment ends using methods or kits (such as the Lucigen DNA terminator End Repair Kit) known in the art to generate ends that are optimal for insertion, for example, into blunt sites of cloning vectors. In a particular embodiment, the fragment ends of the population of nucleic acids are blunt ended. More particularly, the fragment ends are blunt ended and phosphorylated. The phosphate moiety can be introduced during an enzymatic treatment, for example using polynucleotide kinase. It is preferable, in the case of fragments of 50-150 base pairs in size, to do the end repair steps and kinase steps at a low temperature to prevent de-annealing of the target duplex fragments.

In a particular embodiment, the target polynucleotide sequences are prepared with single overhanging nucleotides by, for example, activity of certain types of DNA polymerase such as Taq polymerase or Klenow exo minus polymerase which has a nontemplate-dependent terminal transferase activity that adds a single deoxynucleotide, for example deoxyadenosine (A) to the 3' ends of, for example, PCR products. Such enzymes can be utilised to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase whilst the adaptor polynucleotide construct could be a T-construct with a compatible 'T' overhang present on the 3' terminus of each duplex region of the adaptor construct. This end modification prevents self-ligation of both vector and target such that there is a bias towards formation of the combined ligated adaptor-target sequences. The use of Klenow exo minus polymerase is particularly preferred for the generation of short insert libraries, as the enzyme is a mesophile that operates optimally at 37° C., rather than a thermophile such as Taq that operates at a much higher temperature, which causes a loss of the A/T rich sequences from the library.

The term 'target polynucleotide duplexes' refers to nucleic acid molecules that it is desired to sequence. The term 'template' refers to the target sequences ligated to the adaptor sequences and further amplified by primers hybridised to the adaptors to copy the targets; and thus the 'templates' have known ends suitable for amplification; whereas the 'targets' without the adaptors do not.

The second step of the method comprises ligating a double stranded adaptor polynucleotide sequence to both ends of the target polynucleotide duplexes to form combined ligated adaptor-target-adaptor polynucleotide sequences. It is particularly advantageous to use the same adaptor construct for both ends of the target duplex, although two sets of adaptors can also be utilised.

Ligation methods are known in the art and utilise standard methods (Sambrook and Russell, Molecular Cloning, A Laboratory Manual, third edition). Such methods utilise ligase enzymes such as DNA ligase to effect or catalyse joining of the ends of the two polynucleotide strands of, in this case, the adaptor duplex construct and the target polynucleotide duplexes, such that covalent linkages are formed. The adaptor duplex construct may contain a 5'-phosphate moiety in order to facilitate ligation to the target 3'-OH. The target contains a 5'-phosphate moiety, either residual from the shearing process, or added using an enzymatic treatment step, and has been end repaired, and optionally extended by an overhanging base or bases, to give a 3'-OH suitable for ligation. In this context, joining means covalent linkage of polynucleotide strands which were not previously covalently linked. In a particular aspect of the invention, such joining takes place by formation of a phosphodiester linkage between the two polynucleotide strands, but other means of covalent linkage (e.g. non-phosphodiester backbone linkages) may be used.

Whilst the method of TA ligation (or TA cloning) is known in the art, the presence of the 'T' overhang does not fully remove the formation and presence of adaptor-dimer constructs in the library. The present inventors have made the surprising discovery that during ligation, even with an enzyme which is purported not to have measurable exonuclease activity, the overhanging nucleotide(s) is/are removed from the adaptors with surprising frequency. Thus even with the TA method of cloning, adaptor-dimers are not prevented. The deficiencies of the TA ligation protocol are addressed by the methods disclosed herein.

According to a particular aspect of the invention, in addition to the mismatched region previously described, the adaptor construct or constructs contains an overhanging base or bases at the 3'-end of one of the strands that is complementary to the overhanging base or bases at the 3'-end of the target duplexes, and a 5'-phosphate moiety on the complementary hybridised strand. The adaptor constructs may also contain a region on one, or both, of the strands that does not hybridise with a sequence on the other strand of the adaptor. Such 'mismatched' adaptors can serve as priming sites for further amplification reactions, and may allow for amplification with primers extending beyond the sequence of the ligated adaptor. Thus the region of known sequence in the template for amplification may be longer than the adaptor sequence ligated to the target.

The library of template polynucleotide molecules is particularly suitable for use in solid phase sequencing methods. Because sequence reads may be short, that is around 25-50 base pairs in length, unlike conventional methods of library preparation, it is of no consequence if multiple different target polynucleotide duplexes are ligated into a single template polynucleotide. Because the sequence read is shorter than the length of the individual target polynucleotide duplexes, there is no risk of artificial concatamers of sequence data being produced. The formation of target concatamers is minimised by the presence of an excess of the adaptor constructs.

Optionally the combined ligated polynucleotide sequences and unligated adaptor polynucleotide constructs may be purified from any components of the ligation reaction, such as enzymes, buffers, salts and the like. Suitable purification methods are known in the art and utilise standard methods (Sambrook and Russell, Molecular Cloning, A Laboratory Manual, third edition).

In a next step according to the invention an amplification reaction is optionally prepared. The contents of an amplification reaction are known by one skilled in the art and include appropriate substrates (such as dNTPs), enzymes (e.g. a DNA polymerase) and buffer components required for an amplification reaction. Generally amplification reactions require at least two amplification primers, often denoted 'forward' and 'reverse' primers (primer oligonucleotides) that are capable of annealing specifically to a part of the polynucleotide sequence to be amplified under conditions encountered in the primer annealing step of each cycle of an amplification reaction. In certain embodiments the forward and reverse primers may be identical. Thus the primer oligonucleotides must include an 'adaptor-target specific portion', being a sequence of nucleotides capable of annealing to a part of, that is, a primer-binding sequence, in the polynucleotide molecule to be amplified (or the complement thereof if the template is viewed as a single strand) during the annealing step.

In the context of the present invention, the term 'polynucleotide molecule to be amplified' refers to the original or starting adaptor-target-adaptor sequence added to the amplification reaction. The 'adaptor-target specific portion' in the forward and reverse amplification primers refers to a sequence capable of annealing to the original or initial adaptor-target-adaptor present at the start of the amplification reaction and reference to the length of the 'adaptor-target specific portion' relates to the length of the sequence in the primer which anneals to the starting adaptor-target. It will be appreciated that if the primers contain any nucleotide sequence which does not anneal to the starting adaptor-target in the first amplification cycle then this sequence may be copied into the amplification products (assuming the primer does not contain a moiety which prevents read-through of the polymerase). Hence the amplified template strands produced in the first and subsequent cycles of amplification may be longer than the starting adaptor-target strands. The invention may optionally include the use of forward and reverse primers of sufficient length to hybridise to the whole of the adaptor sequence and at least one base of the target sequence. The forward and reverse primers may also contain a region that extends beyond the adaptor construct, and therefore the amplification primers may be at least 20-100 bases in length. The forward and reverse primers may be of significantly different lengths; for example one may be 20-40 bases, and one may be 40-100 bases in length. The nucleotide sequences of the adaptor-target specific portions of the forward and reverse primers are selected to achieve specific hybridisation to the adaptor-target sequences to be amplified under the conditions of the annealing steps of the amplification reaction, whilst minimising non-specific hybridisation to any other target sequences present. Skilled readers will appreciate that it is not strictly required for the adaptor-target specific portion to be 100% complementary, a satisfactory level of specific annealing can be achieved with less than perfectly complementary sequences. In particular, one or two mis-matches in the adaptor-target specific portion can usually be tolerated without adversely affecting specificity for the template. Therefore the term 'adaptor-target specific portion' should not be interpreted as requiring 100% complementarity with the adaptor-target. However, the requirement that the primers do not anneal non-specifically to regions of the adaptor-target other than their respective primer-binding sequences must be fulfilled.

Amplification primers are generally single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand.

Primers may additionally comprise non-nucleotide chemical modifications, again provided such that modifications do not prevent primer function. Modifications may, for example, facilitate attachment of the primer to a solid support, for example a biotin moiety. Certain modifications may themselves improve the function of the molecule as a primer, or may provide some other useful functionality, such as providing a site for cleavage to enable the primer (or an extended polynucleotide strand derived therefrom) to be cleaved from a solid support.

To reduce the amplification of ligated adaptor-dimers, the present inventors have made the discovery that the forward and reverse amplification primers should anneal to at least one base 'originating' from the target nucleic acid fragment (described below). See FIG. 1. Such a base, or bases, can be part of the sequence of the target nucleic acid fragment, such as for example genomic sequence, or may be attached by a nucleotide tailing reaction, or by a ligation reaction and a subsequent cleavage reaction, for example with a restriction endonuclease. Attachment of a single nucleotide 3'-overhang is preferred. Accordingly the forward and reverse primers therefore contain the complementary base to the nucleotide triphosphate used in the target tailing reaction. The use of dATP in the enzymatic tailing reaction of the target nucleic acids means that the primers should contain a single 3'-'T' overhang. This base can be chemically introduced during primer synthesis, or introduced enzymatically in a similar tailing reaction used to tail the blunt ended target nucleic acids. For the avoidance of doubt, any bases added to the target in treatment steps carried out before the adaptor ligation step are considered to originate from the attached target during the adaptor attachment process.

In order to accurately copy the target DNA sequence, it is desirable to use a DNA polymerase with a high fidelity. Such high fidelity polymerases often have a 'proofreading' exonuclease domain to read and remove incorrectly incorporated nucleotides. Such high fidelity polymerases include Phusion™ DNA polymerase, PfuUltra™ DNA polymerase, Deep Vent® DNA polymerase or KOD DNA polymerase. The forward and reverse amplification primers, as described herein, may be designed such that the 3'-terminal base of the primers only hybridises to constructs that contain the target nucleic acid sequence, and not to adaptor dimers. This reduces amplification of the adaptor dimers, which is desirable to lower the number of adaptor-dimers from the template library. Not wishing to be bound by hypothesis, it is believed that since the primers have an additional 3' terminal base which only hybridises to the target nucleic acid sequence, and because such a base is not present in the adaptor-dimers, the 3' end of the primer forms a mismatched end when hybridised to an adaptor-primer. The efficiency of the polymerase to extend this mis-matched end during amplification appears to be reduced. Hence the efficiency of amplification of adaptor-dimers is also reduced and the number of adaptor-primers contaminating a library is similarly lowered.

Exonuclease activity of some polymerase enzymes used in an amplification reaction may, however, remove the terminal non hybridised bases from the amplification primers. This has the effect that amplification of the adaptor-dimers can occur, albeit at a reduced level. Therefore the amplification primers may be modified to prevent removal of nucleotides from the 3'-end.

In a particular embodiment, the modification is a chemical modification. Exonucleoytic attack on the primer molecules can be efficiently prevented by the introduction of a single phosphorothioate bond at their 3'-termini (Nucleic Acids Research, 1992, 29, (14), 3551-4). Other such exonuclease resistant modifications may include phosphorodithioates, methyl phosphonates and 2'-O-methyl sugars, either separately or in combination. A number of other modifications are known to reduce the exonuclease degradation of single DNA strands, including phosphoramidites (P—NR2), phosphorofluoridates (P—F), boranophosphanes (P—BH3) or phosphoroselenoates (P—Se), and modifications to the sugar rings, such as 2'-O alkyl groups, 2'-fluoro groups, 2'-amino groups such as 2-amino propyl (PNAS, 1999, 96 (25) p 14240-45) or locked nucleic acids (LNA) where the 2' and 4' sugar positions are connected.

The amplification primers or adaptor constructs can optionally be treated with an exonuclease enzyme, for example a DNA polymerase with exonuclease activity, or exonuclease I, prior to use in the amplification reaction. In the case of the phosphorothioate modifications this removes the synthetic failure phosphate sequences, and also the phosphorothioate isomer that remains susceptible to exonucleolysis. The remaining material can be re-purified, if desired, then used in the amplification reaction. Such material is thereby completely resistant to exonucleolysis in the amplification reaction. Therefore the ability of the ligated adaptor-dimers to amplify is significantly reduced or even prevented, and they are thus removed from the library of ligated material. The result is that the efficiency of both amplification and/or sequencing of a library prepared according to the methods of the invention is significantly improved. This results in both a reduction of the costs of sequencing whilst increasing the quantity of useful sequence data.

The processes of exonuclease treatment of the adaptor construct prior to ligation, to prevent the formation of the adaptor-dimers, and the exonuclease treatment of the amplification primers that overlap the target, to prevent amplification of the adaptor dimers may be combined.

Use of the Template Library

Template libraries prepared using any of the methods of the invention may be used in essentially any method of nucleic acid analysis which requires further amplification of the templates and/or sequencing of the templates or amplification products thereof. Exemplary uses of the template libraries include, but are not limited to, providing templates for whole genome amplification and also solid-phase PCR amplification or solid-phase isothermal amplification (of either monotemplate or complex template libraries). A particularly preferred use is in whole-genome amplification carried out on a solid-support.

Whole-Genome Amplification

Template libraries prepared according to the methods of the invention starting from a complex mixture of genomic DNA fragments representing a whole or substantially whole genome provide suitable templates for so-called 'whole-genome' amplification. The term 'whole-genome amplification' refers to a nucleic acid amplification reaction (e.g. PCR) in which the template to be amplified comprises a complex mixture of nucleic acid fragments representative of a whole (or substantially whole) genome.

Solid-Phase Amplification

Once formed, the library of templates prepared according to the methods described above can be used for solid-phase nucleic acid amplification.

Thus, in further aspects the inventions provide use of the methods in solid-phase nucleic acid amplification of template polynucleotide molecules which comprises: preparing a library of template polynucleotide molecules which have common sequences at their 5' and 3' ends using a method according to the first, second or third aspects of the invention described herein and carrying out a solid-phase nucleic acid amplification reaction wherein said template polynucleotide molecules are amplified.

The term 'solid-phase amplification' as used herein refers to any nucleic acid amplification reaction carried out on or in association with a solid support such that all or a portion of the amplified products are immobilised on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilised on the solid support. Solid phase PCR covers systems such as emulsions, wherein one primer is anchored to a bead and the other is in free solution, and colony formation in solid phase gel matrices wherein one primer is anchored to the surface, and one is in free solution.

Although the invention encompasses 'solid-phase' amplification methods in which only one amplification primer is immobilised (the other primer usually being present in free solution), the solid support may be provided with both the forward and the reverse primers immobilised. In practice, there will be a 'plurality' of identical forward primers and/or a 'plurality' of identical reverse primers immobilised on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example one type of primer may contain a non-nucleotide modification which is not present in the other.

In other embodiments of the invention the forward and reverse primers may contain template-specific portions of different sequence.

In all embodiments of the invention, primers for solid-phase amplification are preferably immobilised by covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatisation or functionalisation applied to it. The primer itself may include a moiety, which may be a non-nucleotide chemical modification, to facilitate attachment. In one particularly preferred embodiment the primer may include a sulphur-containing nucleophile, such as phosphorothioate or thiophosphate, at the 5' end. In the case of solid-supported polyacrylamide hydrogels (as described below), this nucleophile will bind to a bromoacetamide group present in the hydrogel. A more particular means of attaching primers and templates to a solid support is via 5' phosphorothioate attachment to a hydrogel comprised of polymerised acrylamide and N-(5-bromoacetamidylpentyl) acrylamide (BRAPA).

The library may be amplified on beads wherein each bead contains a forward and reverse amplification primer. In a particular embodiment, the library of templates is prepared according to the first, second or third aspects of the invention to prepare clustered arrays of nucleic acid colonies, analogous to those described in WO 00/18957 and WO 98/44151, by solid-phase amplification and more particularly solid phase isothermal amplification. The terms 'cluster' and 'colony' are used interchangeably herein to refer to a discrete site on a solid support comprised of a plurality of identical immobilised nucleic acid strands and a plurality of identical immobilised complementary nucleic acid strands. The term 'clustered array' refers to an array formed from such clusters or colonies. In this context the term 'array' is not to be understood as requiring an ordered arrangement of clusters.

The term solid phase, or surface, is used to mean either a planar array wherein primers are attached to a flat surface, for example glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in patent WO9844151, or a process whereby the temperature is maintained as a constant, and the cycles of extension and denaturing are performed using changes of reagents. Such isothermal amplification methods are described in patent application number U.S. 60/783,618 (Isothermal methods for creating clonal single molecule arrays). Due to the lower temperatures required in the isothermal process, this is particularly preferred.

Use in Sequencing/Methods of Sequencing

The invention also encompasses methods of sequencing amplified nucleic acids generated by whole genome or solid-phase amplification. Thus, the invention provides a method of nucleic acid sequencing comprising amplifying a library of nucleic acid templates using whole genome or solid-phase amplification as described above and carrying out a nucleic acid sequencing reaction to determine the sequence of the whole or a part of at least one amplified nucleic acid strand produced in the whole genome or solid-phase amplification reaction.

Sequencing can be carried out using any suitable sequencing technique, wherein nucleotides are added successively to a free 3' hydroxyl group, resulting in synthesis of a polynucleotide chain in the 5' to 3' direction. The nature of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also within the scope of the invention, as are techniques using detection of pyrophosphate release (pyrosequencing). Such pyrosequencing based techniques are particularly applicable to sequencing arrays of beads where the beads have been amplified in an emulsion such that a single template from the library molecule is amplified on each bead.

The initiation point for the sequencing reaction may be provided by annealing of a sequencing primer to a product of the whole genome or solid-phase amplification reaction. In this connection, one or both of the adaptors added during formation of the template library may include a nucleotide sequence which permits annealing of a sequencing primer to amplified products derived by whole genome or solid-phase amplification of the template library.

The products of solid-phase amplification reactions wherein both forward and reverse amplification primers are covalently immobilised on the solid surface are so-called 'bridged' structures formed by annealing of pairs of immobilised polynucleotide strands and immobilised complementary strands, both strands being attached to the solid support at the 5' end. Arrays comprised of such bridged structures provide inefficient templates for nucleic acid sequencing, since hybridisation of a conventional sequencing primer to one of the immobilised strands is not favoured compared to annealing of this strand to its immobilised complementary strand under standard conditions for hybridisation.

In order to provide more suitable templates for nucleic acid sequencing it is preferred to remove substantially all or at least a portion of one of the immobilised strands in the 'bridged' structure in order to generate a template which is at least partially single-stranded. The portion of the template which is single-stranded will thus be available for hybridisation to a sequencing primer. The process of removing all or a portion of one immobilised strand in a 'bridged' double-stranded nucleic acid structure may be referred to herein as 'linearisation'.

Bridged template structures may be linearised by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease (for example 'USER', as supplied by NEB, part number M5505S), or by exposure to heat or alkali, cleavage of ribonucleotides incorporated into amplification products otherwise comprised of deoxyribonucleotides, photochemical cleavage or cleavage of a peptide linker.

It will be appreciated that a linearization step may not be essential if the solid-phase amplification reaction is performed with only one primer covalently immobilised and the other in free solution.

In order to generate a linearised template suitable for sequencing it is necessary to remove 'unequal' amounts of the complementary strands in the bridged structure formed by amplification so as to leave behind a linearised template for sequencing which is fully or partially single stranded.

Most preferably one strand of the bridged structure is substantially or completely removed.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution or heat, will be apparent to the skilled reader with reference to standard molecular biology protocols (Sambrook et al., 2001, *Molecular Cloning, A Laboratory Manual,* 3rd Ed, Cold Spring Harbor Laboratory Press, Cold Spring Harbor Laboratory Press, NY; Current Protocols, eds Ausubel et al.).

Denaturation (and subsequent re-annealing of the cleaved strands) results in the production of a sequencing template which is partially or substantially single-stranded. A sequencing reaction may then be initiated by hybridisation of a sequencing primer to the single-stranded portion of the template.

Thus, the invention encompasses methods wherein the nucleic acid sequencing reaction comprises hybridising a sequencing primer to a single-stranded region of a linearised amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

In a particular sequencing method which can be used in accordance with the invention, the method relies on the use of modified nucleotides having removable 3' blocks, for example as described in WO04018497. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may carry a label to facilitate their detection. In a particular embodiment, the label is a fluorescent label. Each nucleotide type may carry a different fluorescent label, for example as described in U.S. Provisional Application No. 60/801,270 (Novel dyes and the use of their labelled conjugates). However the detectable label need not be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in U.S. Provisional Application No. 60/788,248 (Systems and devices for sequence by synthesis analysis).

The invention is not intended to be limited to use of the sequencing method outlined above, as essentially any sequencing methodology which relies on successive incorporation of nucleotides into a polynucleotide chain can be used. Suitable alternative techniques include, for example, Pyrosequencing™, FISSEQ (fluorescent in situ sequencing), MPSS and sequencing by ligation-based methods.

The target polynucleotide to be sequenced using the method of the invention may be any polynucleotide that it is desired to sequence. Using the template library preparation method described in detail herein it is possible to prepare template libraries starting from essentially any double or single-stranded target polynucleotide of known, unknown or partially known sequence. With the use of clustered arrays prepared by solid-phase amplification it is possible to sequence multiple targets of the same or different sequence in parallel.

The invention will be further understood with reference to the following non-limiting experimental example:

EXAMPLE 1

The following experimental details describe the complete exposition of one embodiment of the invention as described above. The DNA source used is purified BAC DNA. The BAC was produced by cloning a 140k human Chromosome 6 insert into a pTARBAC vector.

The DNA is first prepared for the ligation reaction to the mismatched adaptor by: fragmentation of the DNA by nebulisation, polishing of the DNA ends to make them blunt-ended and phosphorylated, then the addition of a single 'A' nucleotide onto the 3' ends of the DNA fragments. The ligation reaction is performed with the prepared fragmented DNA and adaptor preformed by annealing 'Oligo A' and 'Oligo B' (sequences given below). The product of the reaction is isolated purified from unligated adaptor by gel electrophoresis. Finally, the product of the ligation reaction is subject to cycles of PCR to selectively amplify ligated product that contains adaptor at both ends of the fragments.

Nebulization

Materials

| | | |
|---|---|---|
| BAC DNA (0.116 mg/ml) | | |
| Buffer | Glycerol | 53.1 ml |
| | Water | 42.1 ml |
| | 1M TrisHCl pH 7.5 | 3.7 ml |
| | 0.5M EDTA | 1.1 ml |
| Nebulizer | Invitrogen (#K7025-05) | |
| Qiagen columns | PCR purification kit (#28104) | |

Mix 43 μl (5 micrograms) of DNA
707 μl Buffer

```
                                              (SEQ ID NO: 1)
Oligo A: 5'ACACTCTTTCCCTACACGACGCTCTTCCGATCxT
(x = phosphorothioate bond)

Oligo B:
                                              (SEQ IN NO: 2)
5'Phosphate-GATCGGAAGAGCTCGTATGCCGTCTTCTGCTTG
```

Procedure:

Chill the DNA solution on ice. Assemble a nebulizer and chill on ice. Add the sample of DNA to the nebulizer and chill on ice. Connect tubing from the outlet port of an Argon gas cylinder to the inlet port on the top of the nebulizer and secure with the small plastic clamp. Make sure that the lid of the nebulizer is not turned tight but a bit loose instead and make sure the nebulizer is buried in ice in an ice-bucket and placed in the fume hood. Open the gas cylinder valve to give at least 32 psi of pressure. Nebulize for 5 to 6 minutes. Spin down the nebulizer at 1000 rpm for 1 min in a bench-top centrifuge using a used nebulizer as a balance. Measure the recovered volume—usually somewhere between 400 and 600 µl. Split into 3 aliquots and purify with a Qiagen PCR-purification kit, but using only one column, and finally eluting in 30 µl of EB (Qiagen).

End-Repair
Materials

| T4 DNA Polymerase | NEB #M0203S |
|---|---|
| 10xNEB 2 buffer | NEB #M7002S |
| 100x BSA | NEB #M9001S |
| dNTPs mix (each @ 10 mM) | NEB #N0447S |
| E. coli DNA Pol I large fragment (Klenow) | NEB #M0210S |
| T4 polynucleotide kinase | NEB #M0201S |
| T4 PNK buffer | NEB #M0201S |
| 100 mM ATP | |
| Qiagen columns | PCR purification kit (#28104) |

End repair as follows:

| DNA | 30 µl |
|---|---|
| Water | 12 µl |
| 10xNEB2 | 5 µl |
| 100xBSA | 0.5 µl |
| 10 mM dNTPs | 2 µl |
| T4 DNA pol (3 U/ul) | 5 µl |
| | 50 µl total |

Incubate for 15 min @ room temperature. Add 1 µl of E. coli DNA Pol I large fragment (Klenow) and continue to incubate for a further 15 min at room temperature. Purify the DNA from enzymes, buffer, etc by loading the reaction mix on a Qiagen column, finally eluting in 30 µl EB. The 5' ends of the DNA are then phosphorylated using polynucleotide kinase as follows:

| DNA | 30 µl |
|---|---|
| Water | 9.5 µl |
| 10xPNK buffer | 5 µl |
| 100 mM ATP | 0.5 µl |
| T4 PNK (10 U/ul) | 5 µl |
| | 50 µl total |

Incubate for 30 min @ 37° C. Purify the DNA from enzymes, buffer, etc by loading the reaction mix on a Qiagen column, finally eluting in 30 µl EB.

A—Tailing Reaction
Materials

| Klenow exo⁻ | NEB #M0212S |
|---|---|
| 10x thermopol buffer | NEB #B9004S |
| 1 mM dATP | Amersham-Pharmacia #272050 |
| Qiagen MinElute™ column | PCR purification kit (#28004) |

Prepare the following reaction mix

| DNA | 30 µl |
|---|---|
| 10x NEB2 buffer | 5 µl |

-continued

| 1 mM dATP | 10 µl |
|---|---|
| Klenow exo⁻ (5 U/ul) | 3 µl |
| | ~50 µl total |

Incubate for 30 min @ 37° C., then purify the DNA from enzymes, buffer, etc by loading the reaction mix on a Qiagen MinElute™ column, finally eluting in 10 µl EB.

Anneal Fork Duplex
Materials
'Oligo A' and 'Oligo B'
50 mM Tris/50 mM NaCl pH7
PCR machine

| 100 uM Oligo A | 20 µl |
|---|---|
| 100 um Oligo B | 20 µl |
| Tris/NaCl | 10 µl |
| | 50 µl @ 40 µM duplex in 10 mM Tris/10 mM NaCl pH 7.5 |

Anneal in a PCR machine programmed as follows:
Ramp @ 0.5° C./sec to 97.5° C.
Hold @ 97.5° C. for 150 sec
Then a step of 97.5° C. for 2 sec with a temperature drop of 0.1° C./cycle for 775 cycles Ligation Reaction
Materials

| 40 µM forked adaptor | |
|---|---|
| A-tailed genomic DNA | |
| Quick Ligase | NEB #M2200L |
| Quick Ligase 2x buffer | NEB #M2200L |
| PCR machine | |
| Qiagen columns | PCR purification kit (#28104) |
| DNA | 10 µl |
| 2x buffer | 25 µl |
| 40 uM adaptor | 10 µl |
| Quick Ligase | 5 µl |
| | ~50 µl total |

Incubate for 20 min @ room temperature then purify the DNA from enzymes, buffer, etc by loading the reaction mix on a Qiagen column, finally eluting in 30 µl EB.

Gel Purification
Materials
Agarose Ultra-grade Biorad #161-3107
100 base pair ladder NEB #N3231L
TAE
Loading buffer (50 mM Tris pH8, 40 mM EDTA, 40% w/v sucrose)
Ethidium bromide
Gel trays and tank. Electrophoresis unit Prepare a 2% agarose gel containing ethidium bromide and load the entire sample from the purified ligation reaction in one lane of a gel. Run at 120 V for 50 min, then view the gel on a 'White-light' box. Excise a chunk of gel from 110 bp to approx 170 bp, and purify with a Qiagen Gel purification kit. Two columns may be needed if the gel slice is too big. If using one column then elute in 30 µl EB; if two columns are needed, use the minElute™ columns, elute each in 15 µl EB and pool.

PCR Amplification
Materials
  Ligate DNA

```
PRIMER 1:
                                      (SEQ ID NO: 3)
AATGATACGGCGACCACCGAGATCTACACTCTTTCCCTACACGA

PRIMER 2:
                                      (SEQ ID NO: 4)
CAAGCAGAAGACGGCATACGA
```

2× Phusion™ HF polymerase NEB (#F-531L)
PCR machine
Qiagen MinElute™ columns
  Qiagen (#28004)

Make a 25 fold dilution of the DNA, then prepare a PCR reaction mix as follows:

| | |
|---|---|
| DNA | 1 µl |
| 2x Phusion Master mix | 25 µl |
| 25 uM P5 | 1 µl |
| 25 uM P7 | 1 µl |
| Water | 22 µl |
| | ~50 µl total |

Thermocycle in a PCR machine under the following conditions:
  30 sec @ 98° C.
  [10 sec@ 98° C., 30 sec@ 65° C., 30 sec @ 72° C.] 18 cycles
  5 min @ 72° C.
  Hold @ 4° C.

Purify the DNA from enzymes, buffer, etc by loading the reaction mix on a Qiagen MinElute™ column and elute in 10 µl EB. The DNA library is then ready for amplification on a surface PCR platform.

Validation of Library

1 µl of the DNA library was cloned into a plasmid vector and plated out on agar. 16 colonies were picked, mini-prepped and the cloned inserts sequenced by conventional Sanger sequencing. The sequence data shown below indicates the full length size of the fragment which includes the 5' and 3' adaptors. For sequence 1, for example, the total length of the fragment was 148 bp and the insert size was 56 bp. The sequence data was as follows:

```
1 (148 bp)        Insert: 56 bp
                                      (SEQ ID NO: 5)
AATGATACGGCGACCACCGAGATCTACACTCTTTCCCTACACGACGCTCT
TCCGATCTGAGACGGGGTTTCACCGTTTTAGCCGGGATGGTCTCGATCTC
CTGACCTCGTGATCAGATCGGAAGAGCTCGTATGCCGTCTTCTGCTTG 2 (141 bp)        Insert: 49 bp
                                      (SEQ ID NO: 6)
AATGATACGGCGACCACCGAGATCTACACTCTTTCCCTACACGACGCTCT
TCCGATCTAAGTTTTTACTGTATTTTAAGAATAAGCTCGGCCGAGCGCGG
TGGCTCAAGATCGGAAGAGCTCGTATGCCGTCTTCTGCTTG 3 (175 bp)        Insert: 83 bp
                                      (SEQ ID NO: 7)
AATGATACGGCGACCACCGAGATCTACACTCTTTCCCTACACGACGCTCT
TCCGATCTAGCTGCTTGGGAGGCTGAGGCAGGAGAATCGCTTGAACCTGG
GAGGCAGAGTTTGCAGTGAGCAGAGATTATGCCACTGCACTAGATCGGAA
GAGCTCGTATGCCGTCTTCTGCTTG 4 (161 bp)        Insert: 69 bp
                                      (SEQ ID NO: 8)
AATGATACGGCGACCACCGAGATCTACACTCTTTCCCTACACGACGCTCT
TCCGATCTAAGAGGCTGGAAGCAGAAGAGGTTTCAGACCCAGATCCCTCC
TTTCAGAAAACCCCCCAAACTGAACCAAGATCGGAAGAGCTCGTATGCCG
TCTTCTGCTTG 5 (176 bp)        Insert: 84 bp
                                      (SEQ ID NO: 9)
AATGATACGGCGACCACCGAGATCTACACTCTTTCCCTACACGACGCTCT
TCCGATCTCATCAACTTGTGTACCTTGTAACTGTACCACAACAGGTATTT
TAATTTCCAAACTTTTTACTGCCATGACTATACCCTTTGCTGAGATCGGA
AGAGCTCGTATGCCGTCTTCTGCTTG 6 (156 bp)        Insert: 64 bp
                                      (SEQ ID NO: 10)
AATGATACGGCGACCACCGAGATCTACACTCTTTCCCTACACGACGCTCT
TCCGATCTTAGTGTCCCAGAAAGATGAACTATTTTCCTTCTCTACTTGG
TCTGCCCATTTCTACTTCCTGCAGATCGGAAGAGCTCGTATGCCGTCTTC
TGCTTG 7 (154 bp)        Insert: 62 bp, 83532 C to A
                                      (SEQ ID NO: 11)
AATGATACGGCGACCACCGAGATCTACACTCTTTCCCTACACGACGCTCT
TCCGATCTTCACTATTGTTGCCCAGGCTGGAGTGCAGTGGTGCAATCTCG
GCTCACTGCAACTTCCGCCTAGATCGGAAGAGCTCGTATGCCGTCTTCTG
CTTG 8 (134 bp)        Insert: 42 bp
                                      (SEQ ID NO: 12)
AATGATACGGCGACCACCGAGATCTACACTCTTTCCCTACACGACGCTCT
TCCGATCTTGGGATTACAGGCATGAGCCACCACGCCTGGCTGTATTTGTT
AGATCGGAAGAGCTCGTATGCCGTCTTCTGCTTG 9 (151 bp)        Insert: 59 bp
                                      (SEQ ID NO: 13)
AATGATACGGCGACCACCGAGATCTACACTCTTTCCCTACACGACGCTCT
TCCGATCTTCCTTCTGCTTTTTTCTTCACTCGTTTCCCCACAGAGCAAGA
CAAAAGAAGCCGGCAAGAGATCGGAAGAGCTCGTATGCCGTCTTCTGCTT
G 10 (155 bp)       Insert: 63 bp
                                      (SEQ ID NO: 14)
AATGATACGGCGACCACCGAGATCTACACTCTTTCCCTACACGACGCTCT
TCCGATCTGCGGGTATGAACAGTTCGCCTACGACGGCAAGGATTATCTCA
CCCTGAATGAGGACCTGCGCTAGATCGGAAGAGCTCGTATGCCGTCTTCT
GCTTG 11 (167 bp)       Insert: 75 bp
                                      (SEQ ID NO: 15)
AATGATACGGCGACCACCGAGATCTACACTCTTTCCCTACACGACGCTCT
TCCGATCTTTTCCACACATGCTGAAGTTTTCAAGATTTTGATCATTGCCTA
GTATTTTCATTTTCTTACTTTCCGTGAACCTTAAGATCGGAAGAGCTCGT
ATGCCGTCTTCTGCTTG 12 (132 bp)       Insert: 40 bp
                                      (SEQ ID NO: 16)
AATGATACGGCGACCACCGAGATCTACACTCTTTCCCTACACGACGCTCT
TCCGATCTACAAAAGAAATCGGCTGGGCATGATGCATTCATCTGTAGTAG
ATCGGAAGAGCTCGTATGCCGTCTTCTGCTTG 13 (150 bp)       Insert: 58 bp
                                      (SEQ ID NO: 17)
AATGATACGGCGACCACCGAGATCTACACTCTTTCCCTACACGACGCTCT
TCCGATCTAGTATTTTATTGAGGATTTTTGCATTGATGTTCATCAGGGAT
ATTGGCTTAAATTTTCAGATCGGAAGAGCTCGTATGCCGTCTTCTGCTTG 14 (122 bp)       Insert: 30 bp
                                      (SEQ ID NO: 18)
AATGATACGGCGACCACCGAGATCTACACTCTTTCCCTACACGACGCTCT
TCCGATCTCACCACCACACCTGGCTAATTTTATATTTTAGATCGGAAGAG
CTCGTATGCCGTCTTCTGCTTG 15 (139 bp)       Insert: 47 bp
                                      (SEQ ID NO: 19)
AATGATACGGCGACCACCGAGATCTACACTCTTTCCCTACACGACGCTCT
TCCGATCTTATTGTAGAAGGTATCAAAGAGGAATAAGCTCTCCAGCTTGC
ACAGAAGATCGGAAGAGCTCGTATGCCGTCTTCTGCTTG
```

-continued 16 (124 bp)    Insert: 32 bp
(SEQ ID NO: 20)
CAAGCAGAAGACGGCATACGAGCTCTTCCGATCTTCCAGCCTGGGCGACA
GAGCAAGACTCGGCCTAGATCGGAAGAGCGTCGTGTAGGGAAAGAGTGTA
GATCTCGGTGGTCGCCGTATCATT Validation of Libraries by SBS Sequencing Libraries were validated by SBS sequencing. The BAC libraries made using the method detailed were sequenced by SBS sequencing. The protocols for preparing clusters on hydrogel surfaces and performing SBS sequencing are detailed in application WO06064199, the contents of which are specifically incorporated herein by reference. The sequences of 20 base fragments of each cluster were recorded, and the number of times each sequence appeared ('depth') was plotted against the % G/C content of each fragment.

Figure 2:
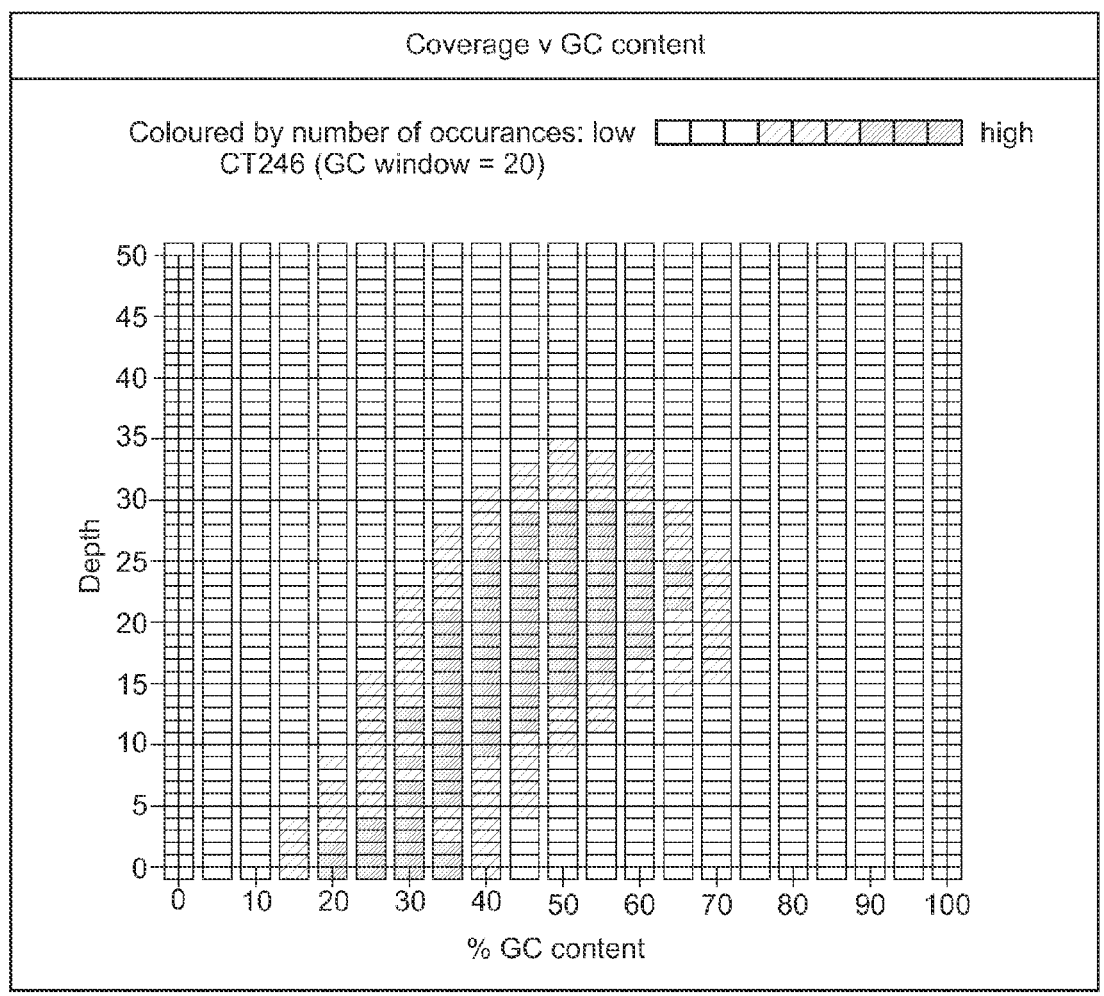
FIG. 2 shows a contour coverage plot of a small insert library generated with elevated temperatures for steps 3 and 4 of the protocol outlined in FIG. 1. The A tailing reaction was performed at 70° C. with Taq polymerase. The increased shading of a box on the graph indicates the abundance of 20 base pair sequences of a certain GC content. The plot indicates that there are a relatively large number of sequences with a GC content around 25% that are poorly represented in the sequenced library data set i.e. low coverage values.

FIG. 2 shows a contour coverage plot of a small insert library generated with elevated temperatures for steps 3 and 4 of the protocol outlined in FIG. 1. The A tailing reaction was performed at 70° C. with Taq polymerase. The increased shading of a box on the graph indicates the abundance of 20 base pair sequences of a certain GC content. The plot indicates that there are a relatively large number of sequences with a G/C content around 25% that are poorly represented in the sequenced library data set i.e. low coverage values.

Figure 3:
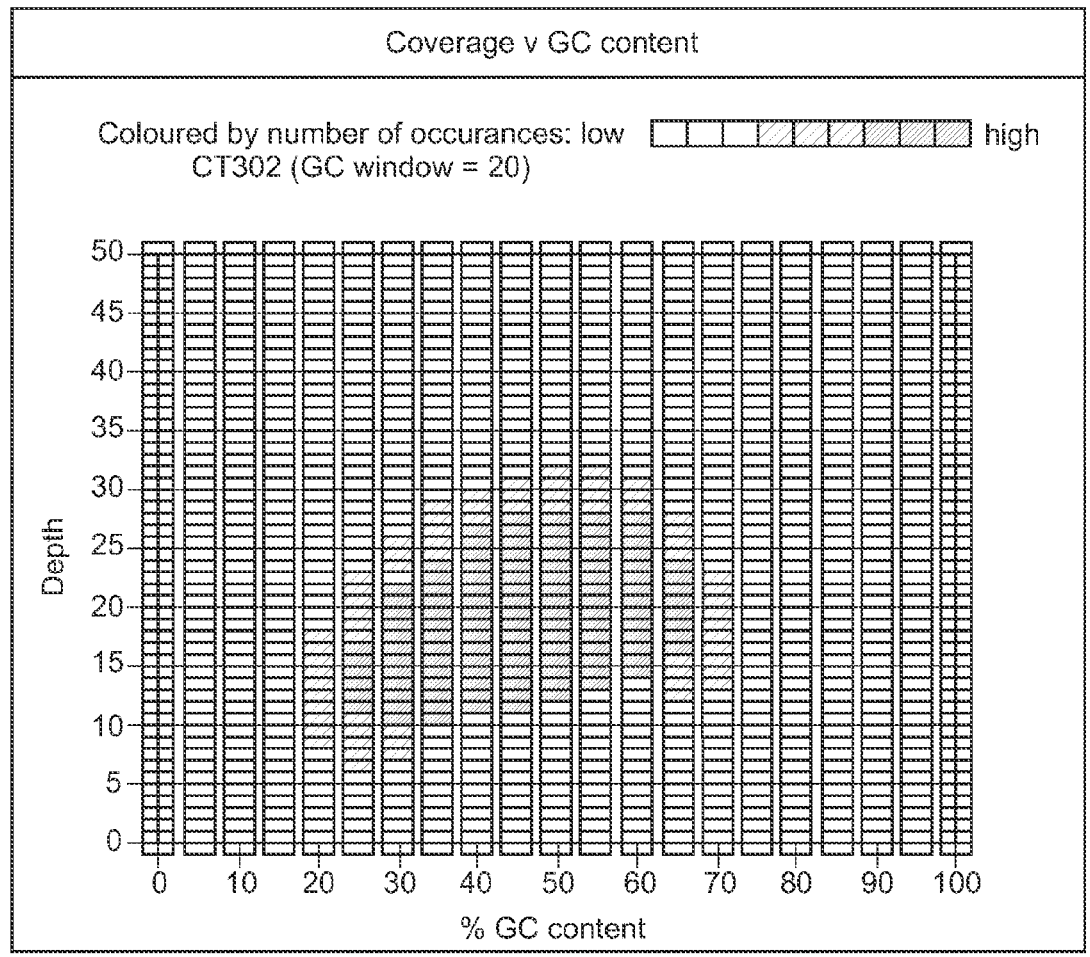
FIG. 3 shows a contour coverage plot of a small insert library generated without elevated temperatures for steps 3 and 4 of the protocol outlined in FIG. 1. The A tailing reaction was performed at 37° C. with Klenow polymerase. The increased shading of a box on the graph indicates the abundance of 20 base pair sequences of a certain GC content. The plot demonstrates that the frequency of sequences with low GC content around 25% is better represented in the sequenced library data set and is represented to almost essentially the same degree as those sequences with a medium to high GC content. In other words the representation of all ranges of GC content is comparable.

FIG. 3 shows a contour coverage plot of a small insert library generated without elevated temperatures for steps 3 and 4 of the protocol outlined in FIG. 1. The A tailing reaction was performed at 37° C. with Klenow exo minus polymerase. The increased shading of a box on the graph indicates the abundance of 20 base pair sequences of a certain GC content. The plot indicates that the frequency of sequences with low GC content around 25% are better represented in the sequenced library data set and are represented to almost the same degree as those sequences with a medium to high GC.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method of solid-phase nucleic acid amplification of template polynucleotide molecules, the method comprising:
   (a) preparing a library of template polynucleotide molecules with common sequences as their 5' ends and common sequences at their 3' ends by:
      (1) providing a plurality of target polynucleotide duplex fragments having a distribution of sequences, and having an average fragment length of less than 150 base pairs;
      (2) treating the plurality of target polynucleotide duplex fragments to phosphorylate the 5' ends of each of the plurality of target polynucleotide duplex fragments and to incorporate a single nucleotide overhang at each of the 3' ends of each of the plurality of short target polynucleotide duplex fragments, wherein the treating produces a plurality of modified target polynucleotide duplex fragments,
         wherein all steps in step (2) are performed at a temperature of less than 65° C.; and
      (3) ligating adaptor polynucleotides to both ends of each of the plurality of modified target polynucleotide duplex fragments to produce a library of template polynucleotide molecules;
         wherein the distribution of sequences in the library of template polynucleotide molecules is essentially equal to the distribution of sequences of the short target polynucleotide duplex fragments; and
   (b) amplifying by solid-phase amplification reaction the template polynucleotide molecules.

2. The method according to claim 1, wherein said template polynucleotide molecules are amplified in an emulsion.

3. The method according to claim 1, wherein said template polynucleotide molecules are amplified with a single primer immobilized on a surface.

4. The method according to claim 3, wherein the surface is a bead or microsphere.

5. The method according to claim 1, wherein said template polynucleotide molecules are amplified using forward and reverse amplification primers immobilized to a surface.

6. The method according to claim 5, wherein said template polynucleotide molecules are amplified by solid-phase isothermal amplification.

7. A method of preparing a library of adaptor-target-adaptor constructs that is representative of a pool of target fragments, said method comprising:
   (a) providing a plurality of target polynucleotide duplex fragments having a distribution of sequences, wherein the target polynucleotide duplex fragments average less than 150 base pairs in length;
   (b) treating the plurality of target polynucleotide duplex fragments to phosphorylate the 5' ends of each of the plurality of target polynucleotide duplex fragments and to incorporate a single nucleotide overhang at each of the 3' ends of each of the plurality of target polynucleotide duplex fragments, wherein the treating produces a plurality of modified target polynucleotide duplex fragments,
      wherein each step in step b) is performed at a temperature of less than 65° C.; and
   (c) ligating adaptor polynucleotides to both ends of each of the plurality of modified target polynucleotide duplex fragments to produce a short insert library of adaptor-target-adaptor constructs;
      wherein the target polynucleotide duplex fragments comprising greater than 50% A/T base pairs are maintained in the library of adaptor-target-adaptor constructs during the steps of the method.

8. The method according to claim 7, wherein said treating is carried out at a temperature of less than 55° C.

9. The method according to claim 7, wherein said adaptor polynucleotides comprise an overhanging end complementary to the modified target polynucleotide duplex fragments.

10. The method according to claim 9, wherein said overhanging end is treated to render the overhanging end resistant to exonucleolysis.

11. The method according to claim 7, further comprising the step of:
   (d) carrying out a primer extension reaction, wherein a first primer oligonucleotide is annealed to an adaptor portion of each of the adaptor-target-adaptor constructs and extended by sequential addition of nucleotides to produce extension products complementary to at least one strand of each of the adaptor-target-adaptor constructs, wherein the extension products have common sequences at their 5' ends.

12. The method according to claim 7, wherein the target polynucleotide duplex fragments are DNA molecules.

13. The method according to claim 12, wherein the target polynucleotide duplex fragments are fragments of genomic DNA or fragments of a whole genome.

14. The method according to claim 7, wherein the target polynucleotide duplex fragments are produced by fragmentation of at least one primary polynucleotide molecule.

15. The method of claim 14, wherein the fragmentation is performed by sonication, nebulization, hydrodynamic shearing, chemical fragmentation, or enzymatic fragmentation.

16. The method according to claim 7, wherein the target polynucleotide duplex fragments are derived from cDNA.

17. The method according to claim 7, further comprising amplifying the adaptor-target-adaptor constructs by a solid-phase amplification reaction.

18. The method according to claim 17, wherein said adaptor-target-adaptor constructs are amplified in an emulsion.

19. The method of claim 17, wherein the solid-phase amplification reaction employs a single primer immobilized on a surface or forward and reverse amplification primers immobilized on a surface.

20. The method according to claim 19, wherein the surface is a bead or microsphere.

21. The method according to claim 19, wherein said adaptor-target-adaptor constructs are amplified by solid-phase isothermal amplification.

* * * * *

UNITED STATES PATENT AND TRADEMARK OFFICE
CERTIFICATE OF CORRECTION

PATENT NO. : 9,902,994 B2
APPLICATION NO. : 14/559548
DATED : February 27, 2018
INVENTOR(S) : Niall Anthony Gormley and Melanie Anne Smith It is certified that error appears in the above-identified patent and that said Letters Patent is hereby corrected as shown below:

In the Claims

In Claim 1, Line 28, delete "short".

Signed and Sealed this
Fifth Day of June, 2018

Andrei Iancu
*Director of the United States Patent and Trademark Office*